US008728503B2

(12) United States Patent
Yamada et al.

(10) Patent No.: US 8,728,503 B2
(45) Date of Patent: *May 20, 2014

(54) EMULSION COSMETIC

(75) Inventors: Kenichi Yamada, Odawara (JP);
Takashi Fukui, Sumida-ku (JP);
Yasushi Haryu, Odawara (JP)

(73) Assignee: KAO Corporation, Tokyo (JP)

( * ) Notice: Subject to any disclaimer, the term of this patent is extended or adjusted under 35 U.S.C. 154(b) by 41 days.

This patent is subject to a terminal disclaimer.

(21) Appl. No.: 13/505,558

(22) PCT Filed: Nov. 5, 2010

(86) PCT No.: PCT/JP2010/069655
§ 371 (c)(1),
(2), (4) Date: May 2, 2012

(87) PCT Pub. No.: WO2011/055771
PCT Pub. Date: May 12, 2011

(65) Prior Publication Data
US 2012/0219608 A1 Aug. 30, 2012

(30) Foreign Application Priority Data

Nov. 6, 2009 (JP) ................. 2009-255092
Nov. 25, 2009 (JP) ................. 2009-267091

(51) Int. Cl.
*A61K 8/02* (2006.01)
*A61K 8/00* (2006.01)

(52) U.S. Cl.
USPC ............................................ 424/401; 424/59

(58) Field of Classification Search
USPC ................................................ 424/401, 59
See application file for complete search history.

(56) References Cited

U.S. PATENT DOCUMENTS

| | | | |
|---|---|---|---|
| 6,132,743 A | 10/2000 | Kuroda et al. | |
| 6,749,838 B1 | 6/2004 | Joichi et al. | |
| 7,563,452 B2 * | 7/2009 | Kuroda et al. | ................. 424/401 |
| 2004/0071956 A1 * | 4/2004 | Tsuji et al. | .................... 428/328 |
| 2004/0081633 A1 * | 4/2004 | Mercier et al. | ............. 424/70.12 |

FOREIGN PATENT DOCUMENTS

| | | |
|---|---|---|
| CN | 1488666 A | 4/2004 |
| JP | 5-139930 | 6/1993 |
| JP | 8 59890 | 3/1996 |
| JP | 2578037 | 2/1997 |
| JP | 11 035440 | 2/1999 |
| JP | 3073887 | 8/2000 |
| JP | 2000 297005 | 10/2000 |
| JP | 2001 58934 | 3/2001 |
| JP | 2001 181136 | 7/2001 |
| JP | 2002 114663 | 4/2002 |
| JP | 2004 189686 | 7/2004 |
| JP | 2006 248999 | 9/2006 |
| JP | 3964780 | 8/2007 |
| JP | 2008 162988 | 7/2008 |
| JP | 2010 241763 | 10/2010 |
| WO | 98 17730 | 4/1998 |
| WO | WO2008034447 | * 3/2008 |

OTHER PUBLICATIONS

JP2000-297005, Machine Translation, 2000.*
International Search Report issued on Feb. 15, 2011 in PCT/JP10/069655 filed on Nov. 5, 2010.
U.S. Appl. No. 13/480,570, filed May 25, 2012, Fukui, et al.
U.S. Appl. No. 13/480,581, filed May 25, 2012, Fukui, et al.
Combined Chinese Office Action and Search Report issued Nov. 28, 2012 in Patent Application No. 201080048816.1 with English Translation.

* cited by examiner

*Primary Examiner* — Blessing M Fubara
*Assistant Examiner* — Jennifer A Berrios
(74) *Attorney, Agent, or Firm* — Oblon, Spivak, McClelland, Maier & Neustadt, L.L.P.

(57) ABSTRACT

Provided is an emulsified cosmetic composition having an excellent UV-protective effect, an excellent transparent feeling, an excellent feeling upon application, and an excellent long-term stability. The emulsified cosmetic composition is characterized by containing a powder which is produced by subjecting a zinc oxide powder (A) having an average particle diameter of 0.1 to 1 μm, an average particle thickness of 0.01 to 0.2 μm, and an average aspect ratio of 3 or more to surface treatment with a silane or silazane compound having a $C_{1-20}$ alkyl or fluoroalkyl group and having reactivity with an inorganic oxide.

10 Claims, 1 Drawing Sheet

EMULSION COSMETIC

CROSS REFERENCE TO RELATED APPLICATION

This application is a 371 of PCT/JP10/069,655, filed on Nov. 5, 2010, and claims priority to the following Japanese Patent Applications: 2009-255092, filed on Nov. 6, 2009; and 2009-267091, filed on Nov. 25, 2009.

FIELD OF THE INVENTION

The present invention relates to an emulsified cosmetic composition having a high UV-protective effect, excellent long-term stability, and an excellent feeling upon application.

BACKGROUND OF THE INVENTION

Recently, it has been pointed out that ultraviolet ray in the UV-A region (320 to 400 nm) penetrates deep into the skin, becoming the main causative factor for photoaging and skin cancer. In view of this, the demand has also risen for cosmetics with a UV-protective effect in the UV-A region.

Conventionally, inorganic powders such as titanium dioxide and zinc oxide have been used for protection against ultraviolet ray. Among them, zinc oxide has recently been frequently used in cosmetics for its relatively high shielding ability against not only the UV-B region (290 nm to 320 nm) but also the UV-A region.

In order to increase the UV-protective effect, fine zinc oxide particles having an average particle diameter of 0.1 μm or less are used. However, these fine zinc oxide particles are prone to aggregate, resulting in poor dispersibility, and when they are blended in a large amount, the resulting cosmetic has poor spreadability, creating unnaturally white spots. For these reasons, the above fine zinc oxide particles are impractical also in terms of usability.

In order to solve the aforementioned problem, for example, there is proposed a stable sunscreen cosmetic composition having an excellent powder dispersibility, a high UV-protective effect, favorable transparency, and a favorable feeling upon application obtained by using a powder produced by subjecting fine zinc oxide particles of 0.1 μm or less to surface treatment with silicic anhydride and then to silicone treatment, and specific polyoxyalkylene-modified polysiloxane (refer to Patent Document 1). However, the above sunscreen cosmetic composition does not have sufficient smooth spreadability, resulting in a poor feeling upon application, and it has insufficient resistance to sweat and water from the external environment. Thus, it is not satisfactory from the viewpoint of cosmetic durability.

Also, a skin external agent in which transparency and a UV-protective effect are improved by using a flaky powder of zinc oxide is proposed (refer to Patent Document 2). However, such the skin external agent has poor dispersibility and is unsatisfactory in terms of unnaturally white spots resulting from blending of the powder and also the feeling upon application.

As a solution to the aforementioned problem, for example, there is proposed a cosmetic composition having an excellent feeling to the touch, high transparency, and an excellent protective capacity against ultraviolet ray obtained by using a flaky powder of zinc oxide having an average particle diameter of 0.1 to 1 μm and fine metal oxide particles having an average particle diameter of 0.001 to 0.1 μm at a specific ratio (refer to Patent Document 3).

Also, there is proposed a cosmetic composition having high transparency and a high UV-protective effect which spreads out well on the skin obtained by using flaky powder of zinc oxide having an average particle diameter of 0.1 to 1 μm and spindle-like or needle-like fine titanium dioxide particles having a minor axis of 0.05 to 0.1 μm and a major axis of 0.01 to 0.5 μm (refer to Patent Document 4).

Further, there is proposed a water-in-oil emulsified cosmetic composition having an excellent feeling upon application and excellent durability obtained by using flaky powder of zinc oxide having an average particle diameter of 0.1 to 1 μm, an average particle thickness of 0.01 to 0.2 μm, and an average aspect ratio of 3 or more, an ether-modified silicone, and a silicone oil (refer to Patent Document 5).

PRIOR ART DOCUMENT

Patent Documents

[Patent Document 1] JP-A-2001-58934
[Patent Document 2] JP-B-3073887
[Patent Document 3] JP-B-3964780
[Patent Document 4] JP-A-11-35440
[Patent Document 5] JP-B-2578037

SUMMARY OF THE INVENTION

The present invention provides an emulsified cosmetic composition characterized by containing a powder which is produced by subjecting a zinc oxide powder (A) having an average particle diameter of 0.1 to 1 μm, an average particle thickness of 0.01 to 0.2 μm, and an average aspect ratio of 3 or more to surface treatment with a silane or silazane compound having a $C_{1-20}$ alkyl or fluoroalkyl group and having reactivity with an inorganic oxide.

Effects of the Invention

The emulsified cosmetic composition of the present invention has not only high transparency and a high UV-protective effect but also favorable long-term stability. Further, it gives no sticky feeling but has a moist feeling, and has an excellent feeling upon application.

EMBODIMENTS FOR CARRYING OUT THE INVENTION

Figure 1:
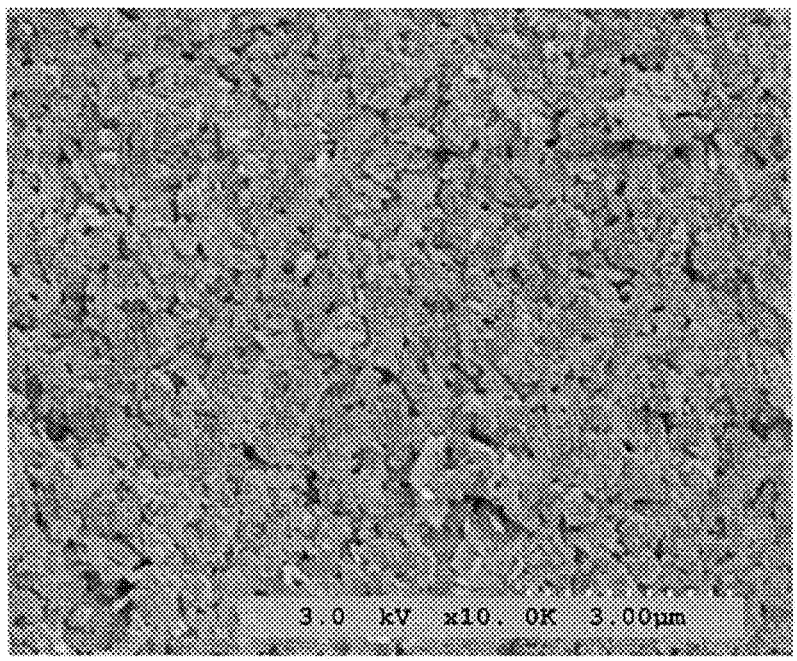
FIG. 1 is a scanning electron microscope image of the coating film of the flaky powder of zinc oxide subjected to surface treatment with alkylsilane (octyltriethoxysilane) obtained in Production Example 2.

However, the aforementioned powder-containing cosmetic composition described in Patent Documents 3 and 4 are effective for obtaining a UV-protective effect while maintaining a certain degree of transparency, but a problem thereof is that when they are prepared as emulsified cosmetic composition, the resulting products have poor long-term stability.

Also, in Patent Document 5, while the water-in-oil emulsified cosmetic composition achieves certain degree of smooth spreadability, it gradually shows reduced spreadability as the volatile components of the emulsified cosmetic composition volatilize and a cosmetic film is formed, which sometimes causes a sudden difficulty of spreading during application of the cosmetic composition. Also, this cosmetic composition is not satisfactory also in terms of long-term stability.

Accordingly, an object of the present invention is to provide an emulsified cosmetic composition excellent in UV-protective effect, transparent feeling, feeling upon application, and long-term stability.

The present inventors conducted intensive research in order to achieve the aforementioned object. As a result, they have found that an emulsified cosmetic composition having not only high transparency and a high UV-protective effect but also excellent long-term stability and an excellent feeling upon application is obtained by using a powder which is produced by subjecting a zinc oxide powder having an average particle diameter of 0.1 to 1 an average particle thickness of 0.01 to 0.2 μm, and an average aspect ratio of 3 or more to surface treatment with a silane or silazane compound having a $C_{1-20}$ alkyl or fluoroalkyl group and having reactivity with an inorganic oxide.

Hereinbelow, the composition of the present invention will be described in detail.

The powder (A) used in the present invention is a powder which is produced by subjecting a zinc oxide powder having an average particle diameter of 0.1 to 1 μm, an average particle thickness of 0.01 to 0.2 μm, and an average aspect ratio of 3 or more (hereinbelow, referred to as a flaky powder of zinc oxide) to surface treatment with a silane or silazane compound having a $C_{1-20}$ alkyl or fluoroalkyl group and having reactivity with an inorganic oxide.

Here, the arithmetic average of the major axis and the minor axis of arbitrary 20 particles present in an arbitrary visual field in a transmission electron micrograph was regarded as the average particle diameter. The average particle thickness was obtained by the arithmetic mean of measured thickness of all of the particles having a measurable thickness in the visual field in the transmission electron micrograph. The average aspect ratio was obtained by (the average particle diameter)/(the average particle thickness), and the resulting value was rounded off to the nearest integer.

As to the form of the flaky powder of zinc oxide used in the present invention, the average particle diameter is 0.1 to 1 μm, preferably 0.1 to 0.8 μm, and more preferably 0.2 to 0.7 μm. When the average particle diameter is less than 0.1 μm, the flaky powder of zinc oxide aggregates, resulting in reduced dispersibility, while when it exceeds 1 μm, the transparency and the ultraviolet ray absorbability are reduced.

The average particle thickness is 0.01 to 0.2 μm, preferably 0.01 to 0.1 μm, and more preferably 0.01 to 0.05 μm. When the average particle thickness is less than 0.01 μm, the flake form is prone to crumble, while the thickness exceeding 0.2 μm results in a feeling of discomfort when the flaky powder of zinc oxide is blended into cosmetic compositions. Thus, an average particle thickness of less than 0.01 μm or more than 0.2 μm is impractical.

The average aspect ratio is 3 or more, preferably 5 or more, and more preferably 7 or more. Also, the upper limit of the average aspect ratio is preferably 30 or less. When the aspect ratio is less than 3, the transparency is reduced.

In the present invention, the flaky powder of zinc oxide preferably further contains a trace element having a valence of +2 or more. Here, the term "contain" means that the trace element is bound to, or retained in, the surface or inside of the flaky powder of zinc oxide.

Examples of the trace element having a valence of +2 or more include metals such as iron, zirconium, calcium, manganese, magnesium, and yttrium. These trace elements can be used alone or a combination of two or more of them can be used, and examples of the combination include zirconium and iron, zirconium and magnesium, iron and magnesium, and iron and calcium. From the viewpoint of the protective capacity against ultraviolet ray, the content of the trace element is preferably 0.005 to 1.0 mole, more preferably 0.01 to 0.5 mole per 100 moles of zinc contained in the flaky powder of zinc oxide.

Here, the content of the element added was obtained by dissolving a predetermined amount of dry powder in 6 N hydrochloric acid, diluting the resulting solution to a predetermined volume, and analyzing it by inductively coupled plasma (ICP) atomic emission spectrometry to obtain the concentrations of zinc and other elements added, and then calculating the mole ratio of the element added to zinc.

Examples of the silane or silazane compound having a $C_{1-20}$ alkyl or fluoroalkyl group and having reactivity with an inorganic oxide used in the present invention include (1) an alkoxysilane or halogenosilane compound having a $C_{1-20}$ alkyl or fluoroalkyl group and (2) a silazane compound having a $C_{1-20}$ alkyl or fluoroalkyl group. Examples of these silane compounds and silazane compounds include a silane compound represented by the following formula (1) and a silazane compound represented by the following formula (2):

$$RR^1{}_nSiX_{3-n} \quad (1)$$

wherein, n is an integer of 0 or 1, R represents a $C_{1-20}$ alkyl or fluoroalkyl group (which may be linear or branched), $R^1$ represents a $C_{1-6}$ alkyl group, and X represents a halogen atom or an alkoxy group, and

$$R^2R^3R^4SiNHSiR^5R^6R^7 \quad (2)$$

wherein, $R^2$ to $R^7$ may represent a $C_{1-20}$ alkyl or fluoroalkyl group (which may be linear or branched) and be the same or different.

In the aforementioned formulas (1) and (2), among the alkyl or perfluoroalkyl groups represented by R and $R^2$ to $R^7$, a $C_{6-10}$ alkyl or perfluoroalkyl group is more preferable, and a hexyl group, an octyl group, a decyl group, an octadecyl group, a trifluoropropyl group, a heptadecafluorodecyl group, and the like are preferable. Examples of $R^1$ include a methyl group, an ethyl group, and a propyl group. Examples of the halogen atom include a chlorine atom and a bromine atom. Examples of the alkoxy group include a $C_{1-6}$ alkoxy group such as a methoxy group, an ethoxy group, and an isopropoxy group.

Specific examples of the silane compound include hexyltrimethoxysilane, octyltrimethoxysilane, decyltrimethoxysilane, octadecyltrimethoxysilane, octyltriethoxysilane, trifluoropropyltrimethoxysilane, and heptadecafluorodecyltrimethoxysilane. Among them, octyltriethoxysilane and octyltrimethoxysilane are particularly preferable. Preferred Examples of the silazane compound include hexamethyldisilazane and octyldisilazane, of which octyldisilazane is more preferable. The above silane or silazane compounds are preferable because they have such characteristics that they can easily be treated uniformly and are easily supplied, and are inexpensive in terms of cost, and further, when a powder (A) having been subjected to surface treatment with these compounds is blended into products, excellent characteristics such as dispersibility are obtained.

Examples of the treatment method of the flaky powder of zinc oxide with the aforementioned silane or silazane compound include a method including allowing a silane or silazane compound to undergo chemical reactions with a reactive group (such as an alkoxy group, halogen, and an amino group) on the surface of a flaky powder of zinc oxide, e.g., a method including mixing a silane or silazane compound and a flaky powder of zinc oxide in an organic solvent such as n-hexane, cyclohexane, and a lower alcohol, and performing pulverization, if necessarily, and then removing the organic solvent by heating or reducing pressure, and applying heat treatment preferably at 80 to 250° C.

Other examples thereof are the method described in JP-A-2007-326902, which includes subjecting a flaky powder of zinc oxide to coating treatment with a specific polysiloxane compound, and then to surface treatment using the aforementioned silane or silazane compound in water.

Examples thereof also include a method including coating the surface of a flaky powder of zinc oxide with an inorganic oxide such as silica, alumina, zirconia, titanium dioxide, iron oxide, and cerium oxide in advance, and then coating the surface of the resulting inorganic oxide-treated flaky powder of zinc oxide with a silane or silazane compound. Examples of the production method of inorganic oxide-treated flaky powder of zinc oxide include previously publicly known treatment methods such as wet processing using a solvent and a mechanochemical method. One example thereof is a method including coating the surface of a flaky powder of zinc oxide with a silicone compound and calcinating the resulting flaky powder of zinc oxide to obtain a silica-coated flaky powder of zinc oxide, which is carried out according to the method described in International Publication No. WO98/17730.

The amount of the silane or silazane compound for coating the flaky powder of zinc oxide is preferably 3 to 15% by weight, more preferably 5 to 10% by weight of the total amount of the flaky powder of zinc oxide used. When the amount of the coating is within the above range, the surface of the flaky powder of zinc oxide is uniformly coated with the silane or silazane compound and the silane or silazane compound is prevented from aggregating or precipitating on the surface of the flaky powder of zinc oxide.

The flaky powder of zinc oxide (A) having been subjected to surface treatment with the silane or silazane compound used in the present invention is contained in an amount of preferably 0.5 to 20% by weight, more preferably 1 to 18% by weight of the total amount of the emulsified cosmetic composition. When the amount of the flaky powder of zinc oxide is within the above range, good powder dispersibility is obtained and also an increase in the viscosity of the preparation can be prevented.

It is more preferable that the emulsified cosmetic composition of the present invention contains, in addition to the aforementioned powder (A), a zinc oxide powder (B) having an average particle diameter of 0.01 to 1 μm (hereinbelow, referred to as a fine particle zinc oxide powder) in order to obtain excellent long-term stability and an excellent feeling upon application, while achieving high transparency and a high UV-protective effect.

The average particle diameter of the fine particle zinc oxide powder (B) used in the present invention is within a range of preferably 0.01 to 1 μm, more preferably 0.012 to 0.2 μm, and even more preferably 0.015 to 0.1 μm. When the above average particle diameter is less than 0.01 μm, the powder becomes highly active and has strong aggregability, and this causes, in many cases, such a powder to substantially behave as a powder having a particle diameter equal to or larger than the applicable range of the present invention as a secondary particle. Also, when the average particle diameter exceeds 1 μm, there may be an optical problem such as the opacification tendency of the preparation.

Examples of the form of the fine particle zinc oxide powder (B) used in the present invention include a spherical form, a rod-like form, a spindle-like form, a needle-like form, and an indeterminate form; however, as long as the average particle diameter is within the aforementioned range, the fine particle zinc oxide powder in any form can be used. However, the fine particle zinc oxide powder having a different form from that of the aforementioned flaky powder of zinc oxide is preferable, and more preferably, the fine particle zinc oxide has preferably an average aspect ratio of less than 3, more preferably 2 or less, and even more preferably 1.5 or less. When the average aspect ratio is within the above range, not only high transparency but also a favorable UV-protective effect is achieved even when it is used in combination with the flaky powder of zinc oxide (A) subjected to surface treatment with the aforementioned silane compound and the like. Also, the form of the fine particle zinc oxide powder (B) is preferably spherical. The above fine particle zinc oxide powder is commercially available as, for example, FINEX-25, FINEX-50, and FINEX-75 (manufactured by Sakai Chemical Industry Co., Ltd.), MZ500 series, MZ700 series (manufactured by Tayca Corporation), and ZnO-350 (manufactured by Sumitomo Osaka Cement Co., Ltd.).

The above fine particle zinc oxide powder is preferably subjected to surface treatment using a silane or silazane compound as in the aforementioned flaky powder of zinc oxide or to the other previously publicly known surface treatment such as fluorine compound treatment, silicone treatment, silicone resin treatment, pendant treatment, silane coupling agent treatment, titanate coupling agent treatment, oil agent treatment, N-acylated lysine treatment, polyacrylic acid treatment, metallic soap treatment, amino acid treatment, inorganic compound treatment, plasma treatment, mechanochemical treatment, in advance.

Examples thereof include surface treatment using methyl hydrogen polysiloxane or the methyl hydrogen polysiloxane-dimethylpolysiloxane copolymer represented by the following formula (3) and surface treatment using a silane or silazane compound as in the aforementioned flaky powder of zinc oxide. Among them, surface treatment using a silane or silazane compound as in the aforementioned flaky powder of zinc oxide is preferred.

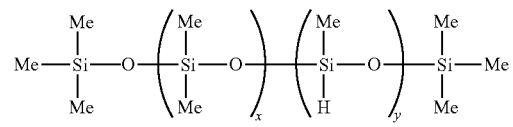

(3)

wherein, x and y are each an integer and $1 \leq x+y \leq 60$.

The fine particle zinc oxide powder (B) used in the present invention is contained in an amount of preferably 0.5 to 20% by weight, more preferably 1 to 18% by weight of the total amount of the emulsified cosmetic composition. When the amount of the fine particle zinc oxide powder (B) is within the above range, good powder dispersibility is obtained and also an increase in the viscosity of the preparation can be prevented.

In the present invention, the total content of the flaky powder of zinc oxide (A) subjected to surface treatment with the silane compound and the like and the fine particle zinc oxide powder (B) is preferably 1 to 30% by weight, more preferably 2 to 20% by weight of the total amount of the emulsified cosmetic composition. When the total content is within the above range, an excellent feeling upon application and good long-term stability are achieved.

In the present invention, the blending ratio (weight ratio) of the flaky powder of zinc oxide (A) subjected to surface treatment with the silane compound and the like to the fine particle zinc oxide (B), (A)/(B), is 1/2 to 10/1, preferably 7/13 to 9/1, more preferably 3/5 to 5/2. When the blending ratio is within the above range, not only high transparency and a high UV-protective effect but also excellent long-term stability and a smooth feel upon application are obtained.

It is preferable that the emulsified cosmetic composition of the present invention contains, in addition to the aforementioned powder (A), a polyether-modified silicone (C) in order to obtain excellent long-term stability, excellent smoothness of the coating film, and durability of the cosmetic effect, while achieving high transparency and a high UV-protective effect. It is to be noted that the aforementioned component (B) may be used in combination with the component (C).

Examples of the polyether-modified silicone (C) include those represented by the following formulas (4) to (6).

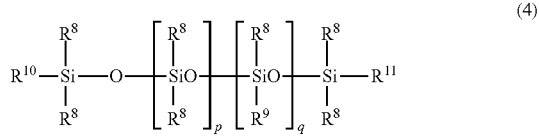
(4)

wherein, $R^8$ represents a $C_{1-5}$ alkyl or phenyl group, $R^9$ represents a group represented by the formula —$(CH_2)_r$—O—$(C_2H_4O)_s$—$(C_3H_6O)_t$—$R^{12}$, wherein $R^{12}$ is a hydrogen atom or a $C_{1-5}$ alkyl group, r is a number of 1 to 5, s is a number of 1 to 50, and t is a number of 0 to 30, and $R^{10}$ and $R^{11}$ represent the same group as either one of $R^8$ and $R^9$, p and q are each an integer, and p=5 to 300 and q=1 to 50, with the proviso that not all of $R^8$ are simultaneously phenyl groups.

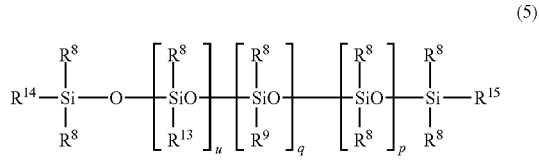
(5)

wherein, $R^8$, $R^9$, p, and q represent the same meaning as above, $R^{13}$ represents a $C_{2-20}$ alkyl group, $R^{14}$ and $R^{15}$ represent the same group as any one of $R^8$, $R^9$ and $R^{13}$, u is an integer and u=1 to 30, with the proviso that not all of $R^8$ are simultaneously phenyl groups.

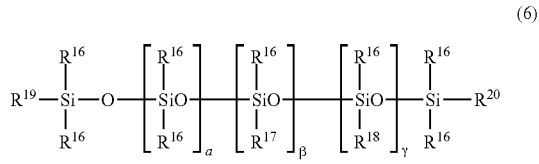
(6)

wherein, $R^{16}$ represents the same or different, unsubstituted or substituted $C_{1-20}$ alkyl or aryl group, $R^{17}$ represents a group represented by the formula -$Q^1$-O—$(C_2H_4O)_x$—$(C_3H_6O)_yR^{21}$, wherein $Q^1$ is a $C_{1-4}$ hydrocarbon group, $R^{21}$ is a hydrogen atom, or a $C_{1-4}$ alkyl or acetyl group, x and y are each an integer and x=0 to 100, y=0 to 100, and x+y≥1, or a $C_{1-10}$ fluorine-substituted alkyl group, $R^{18}$ represents a group represented by the formula -$Q^2$-O—$R^{22}$, wherein $Q^2$ is a $C_{1-4}$ hydrocarbon group and $R^{22}$ is a $C_{8-30}$ hydrocarbon group, or the formula -$Q^3$-O—$(C_2H_4O)_x$—$(C_3H_6O)_yR^{23}$, wherein $Q^3$ is a $C_{2-5}$ hydrocarbon group, $R^{23}$ is a hydrogen atom, a $C_{1-5}$ alkyl, acetyl, phosphate, or sulfate group, or a salt thereof, and x and y are the same as above, $R^{19}$ and $R^{20}$ represent the same group as any one of $R^{16}$, $R^{17}$, and $R^{18}$, and α, β, and γ are each an integer and α=0 to 500, β=1 to 500, and γ=1 to 500.

It is to be noted that the polyether-modified silicone represented by the formulas (4) to (6) has a silicone main chain having a branched structure and may be co-modified with a functional group other than polyether such as perfluoroalkyl without departing from the object of the present invention.

Among the polyether-modified silicones used in the present invention, as a water-in-oil emulsified cosmetic composition, a polyether-modified silicone having an HLB ranging from 4 to 7 is preferable, and perfluoroalkyl/polyoxyalkylene co-modified organopolysiloxane having an HLB ranging from 4 to 7 (for example, a compound represented by the formula (5), wherein $R^{16}$ is the same or different, unsubstituted or substituted $C_{1-20}$ alkyl or aryl group, $R^{17}$ is a $C_{1-10}$ fluorine-substituted alkyl group, $R^{18}$ is the formula -$Q^3$-O—$(C_2H_4O)_x$—$(C_3H_6O)_yR^{23}$, wherein $Q^3$ is a $C_{2-6}$ hydrocarbon group, $R^{23}$ is a hydrogen atom, a $C_{1-5}$ alkyl, acetyl, phosphate, or sulfate group, or a salt thereof, and x and y are each an integer and x=0 to 100, y=0 to 100, and x+y≥1, $R^{19}$ and $R^{20}$ are the same group as any one of $R^{16}$, $R^{17}$, and $R^{18}$, and α, β, and γ are each an integer and α=0 to 500, β=1 to 500, and γ=1 to 500) is more preferable. The perfluoroalkyl/polyoxyalkylene co-modified organopolysiloxane is commercially available as, for example, FPD4970 and FPD6131 (both are manufactured by Shin-Etsu Chemical Co., Ltd.), the values of physical properties for these compounds are shown in Table 1.

TABLE 1

|  | FPD4970 | FPD6131 |
| --- | --- | --- |
| Refractive index (25° C.) | 1.4228 | 1.4168 |
| Viscosity (cs) | 700 | 1320 |
| Specific gravity (25° C.) | 1.041 | 1.035 |
| HLB | 6.1 | 5.3 |

Among the polyether-modified silicones used in the present invention, a polyether-modified silicone having an HLB ranging from 8 to 18 is preferable as an oil-in-water emulsified cosmetic composition.

The polyether-modified silicone (C) in the present invention is contained in an amount of preferably 0.1 to 5% by weight, more preferably 0.3 to 3% by weight of the total amount of the emulsified cosmetic composition. When the content of the polyether-modified silicone is within the above range, excellent storage stability and an excellent feeling upon application can be obtained.

In order to further improve the protective capacity against ultraviolet ray, the emulsified cosmetic composition of the present invention may contain an organic ultraviolet absorber (D). Examples of the organic ultraviolet absorber used in the present invention include 2-hydroxy-4-methoxybenzophenone, 2-hydroxy-4-methoxybenzophenone-5-sulfonic acid, 2,2'-dihydroxy-4,4'-dimethoxybenzophenone, disodium 2,2'-dihydroxy-4,4'-dimethoxy-5,5'-disulfobenzophenone, 2,4-dihydroxybenzophenone, 2,2',4,4'-tetrahydroxybenzophenone, 4-tert-butyl-4'-methoxy-dibenzoylmethane, 2,4,6-trianilino-p-(carbo-2'-ethylhexyl-1'-oxy)-1,3,5-triazine, menthyl anthranilate, 2-(2-hydroxy-5-methylphenyl)benzotriazole, and 2-(4-diethylamino-2-hydroxybenzoyl)-hexyl benzoate.

Among the aforementioned organic ultraviolet absorbers, when 2-(4-diethylamino-2-hydroxybenzoyl)-hexyl benzoate is blended into the emulsified cosmetic composition of the present invention, the resulting emulsified cosmetic composition can achieve a particularly excellent UV-protective effect and a good feeling upon application without a sticky feeling. This 2-(4-diethylamino-2-hydroxybenzoyl)-hexyl benzoate is an organic ultraviolet absorber represented by the following formula (7), and is commercially available as Uvinul A Plus (manufactured by BASF Japan, Ltd.). It absorbs ultraviolet ray within a range of 310 to 390 nm (UV-A region) with a maximum absorption wavelength of approximately 354 nm.

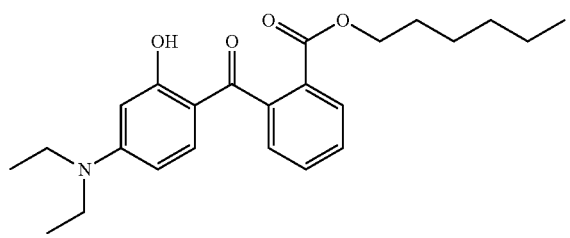

(7)

In the present invention, the content of the organic ultraviolet absorber is preferably 0.01 to 20% by weight, more preferably 0.05 to 10% by weight of the total amount of the emulsified cosmetic composition. When the content of the organic ultraviolet absorber is within the above range, an excellent UV-protective effect and good long-term stability are achieved.

Of the content of the organic ultraviolet absorber, the content of 2-(4-diethylamino-2-hydroxybenzoyl)-hexyl benzoate is preferably 0.01 to 8% by weight, more preferably 0.05 to 3% by weight.

Also, in the present invention, a polymer powder having the aforementioned organic ultraviolet absorber enclosed therein may be used. The polymer powder may or may not be hollow, and the average particle diameter may range from 0.1 to 50 and the particle size distribution may be broad or sharp. Examples of the kind of the polymer include acrylic resin, methacrylic resin, styrene resin, urethane resin, polyethylene, polypropylene, polyethylene terephthalate, silicone resin, nylon, and acrylamide resin. Among these polymer powders, a powder containing organic ultraviolet absorber in an amount of 0.1 to 30% by weight of the powder weight is preferable.

In order to further improve the feeling upon application and the long-term stability, the emulsified cosmetic composition of the present invention may contain various kinds of polysaccharides (E).

Examples of the polysaccharide used in the present invention include pullulan, dextran, cyclosophoran, laminarin, schizophyllan, lentinan, arabinogalactan, barley glucan, lichenan, succinoglycan, xyloglucan, locust bean gum, xanthan gum, chitosan, pustulan, carrageenan, hyaluronic acid, or a salt thereof, and among these, hyaluronic acid, an alkali metal salt of hyaluronic acid, and xanthan gum are preferred.

Hyaluronic acid is a high-viscosity mucopolysaccharide obtained by extraction from the chicken comb or by a fermentation method using modified *Streptococcus Zooepidemicus* or *Streptococcus equi*, which is a species of *Lactococcus*. It is commercially available as hyaluronic acid FCH series (manufactured by Kikkoman Biochemifa Company) and hyaluronic acid liquid HA series (manufactured by Kewpie Corporation).

In the present invention, the content of the aforementioned polysaccharide (E) is preferably 0.0001 to 5% by weight, more preferably 0.001 to 3% by weight of the total amount of the emulsified cosmetic composition. As long as the content of the polysaccharide (E) is within the above range, even when it is used with the flaky powder of zinc oxide and the like, the resulting emulsified cosmetic composition is free from sticky feeling while having good long-term stability.

The emulsified cosmetic composition of the present invention may further contain water, oil components, emulsifiers, and also, as long as the effect of the present invention is not impaired, ingredients which are normally blended into cosmetics such as lower alcohols, fluorine compounds, resin, thickening agents, anti-microbial preservatives, fragrances, humectants, salts, solvents, antioxidants, chelating agents, neutralizers, pH adjusters, insect repellents, and physiologically active ingredients. Here, as the oil component, silicone compounds, higher alcohols, oil and fat, ester oil, hydrocarbon oil, and the like are used. Also, as the emulsifier, various kinds of surfactants are used.

The emulsified cosmetic composition of the present invention may be used as a cosmetic without any particular limitation; however, it is preferably used as a hair cosmetic such as a shampoo, a rinse, and a conditioner, and a skin cosmetic composition such as a facial wash, a cleansing cosmetic composition, a sunscreen cosmetic composition, a facial pack, and a massage cosmetic composition. Among them, it is more preferably to be applied to a sunscreen cosmetic composition, a suntan, a makeup base cosmetic composition, a foundation having a protective capacity against ultraviolet ray, and the like.

Regarding the emulsion type of the emulsified cosmetic composition of the present invention, it is not limited to a water-in-oil emulsified composition, an oil-in-water emulsified composition, or the like but can be applied to various emulsion types. Also, the formulation of the emulsified cosmetic composition of the present invention can be prepared as a liquid, an emulsion, a cream, a paste, a solid, a multilayered form, and the like. It can also be prepared as a sheet, a spray and a mousse.

EXAMPLES

Hereinbelow, the present invention will be described in more detail with reference to Examples; however, the present invention will not be limited by these Examples.

Before describing Examples, the production method of the powder subjected to surface treatment used in the following Examples will be described.

Production Example 1

Production of Flake-Like Zinc Oxide

Into 315 ml of an aqueous solution containing $5 \times 10^{-2}$ mole of sulfuric acid, $1.6 \times 10^{-1}$ mole of zinc sulfate, $3.8 \times 10^{-2}$ mole of sodium sulfate, and, as a salt of a trace element, $1.6 \times 10^{-4}$ mole of ferrous sulfate were dissolved. Subsequently, while stirring the resulting solution at 6000 r.p.m with a homomixer, 230 mL of a 2 N aqueous solution of sodium hydroxide was added over 15 seconds (pH=12.8) to allow precipitate to form, and stirring was continued for 10 minutes. The resulting solution was then matured at 100° C. for 90 minutes, filtered, washed with water, and dried at 230° C. for approximately 10 hours to give an ultraviolet absorptive powder. The thus-obtained powder was observed under a scanning electron microscope and confirmed to be a flake-like particle (with an average particle diameter of 0.25 µm, an average particle thickness of 0.019 µm, an aspect ratio of 13, and a content of iron element of 0.11 mol %).

Production Example 2

Production of a Flaky Powder of Zinc Oxide Subjected to Surface Treatment with Alkylsilane A slurry composed of 93 parts by weight of the flaky powder of zinc oxide, 7 parts by weight of octyltriethoxysilane, and toluene was produced, which was then pulverized and crushed using a bead mill (DYNO-MILL, manufactured by Shinmaru Enterprises Corporation). Subsequently, toluene was distilled off by heating under reduced pressure, and the resulting product was subjected to heat treatment at 150° C. for 4 hours using an air blast stream-type dryer to give an octyltriethoxysilane-treated flake powder of zinc oxide.

Production Example 3

Production of a Flaky Powder of Zinc Oxide Subjected to Surface Treatment with Silicone A slurry composed of 93 parts by weight of the flaky powder of zinc oxide, 7 parts by weight of methyl hydrogen polysiloxane (KF-99P, manufactured by Shin-Etsu Chemical Co., Ltd.), and isopropyl alcohol was produced, which was thoroughly stirred and then pulverized. The solvent was distilled off by heating under reduced pressure, and the resulting product was subjected to heat treatment at 150° C. for 4 hours in the air to give a flaky powder of zinc oxide subjected to surface treatment with methyl hydrogen polysiloxane.

Production Example 4

Production of a Fine Particle Zinc Oxide Powder Subjected to Surface Treatment with Alkylsilane A slurry composed of 93 parts by weight of a fine particle zinc oxide powder (substantially spherical, an average particle diameter of 0.02 µm), 7 parts by weight of octyltriethoxysilane, and toluene was produced, which was then pulverized and crushed using a bead mill (DYNO-MILL, manufactured by Shinmaru Enterprises Corporation). Subsequently, toluene was distilled off by heating under reduced pressure, and the resulting product was subjected to heat treatment at 150° C. for 4 hours using an air blast stream-type dryer to give an octyltriethoxysilane-treated fine particle zinc oxide powder.

Production Example 5

Production of a Fine Particle Zinc Oxide Powder Subjected to Surface Treatment with Silicone A slurry composed of 95 parts by weight of a fine particle zinc oxide powder (substantially spherical, an average particle diameter of 0.02 µm), 5 parts by weight of methyl hydrogen polysiloxane (KF-99P, manufactured by Shin-Etsu Chemical Co., Ltd.), and isopropyl alcohol was produced, which was thoroughly stirred and then pulverized. The solvent was distilled off by heating under reduced pressure, and the resulting product was subjected to heat treatment at 150° C. for 4 hours in the air to give a fine particle zinc oxide powder subjected to surface treatment with methyl hydrogen polysiloxane.

Production Example 6

Production of a Fine Particle Titanium Oxide Powder Subjected to Surface Treatment with Silicone A slurry composed of 95 parts by weight of a fine particle titanium dioxide powder (substantially spherical, an average particle diameter of 0.017 µm) and 5 parts by weight of methyl hydrogen polysiloxane (KF-99P, manufactured by Shin-Etsu Chemical Co., Ltd.), and isopropyl alcohol was produced, which was thoroughly stirred and then pulverized. The solvent was distilled off by heating under reduced pressure, and the resulting product was subjected to heat treatment at 160° C. for 4 hours in the air to give a fine particle titanium dioxide powder subjected to surface treatment with methyl hydrogen polysiloxane.

Test Example 1

To the powders of Production Example 2 and Production Example 3, cyclomethicone was added, and the powders were dispersed by a disperser, whereby samples each having a powder content of 10% by weight were produced. These samples were applied onto glass plates to form a film with a thickness of 6 µm using a doctor blade (YD model), and after drying, images were taken with scanning electron microscope (SEM).

Figure 2:
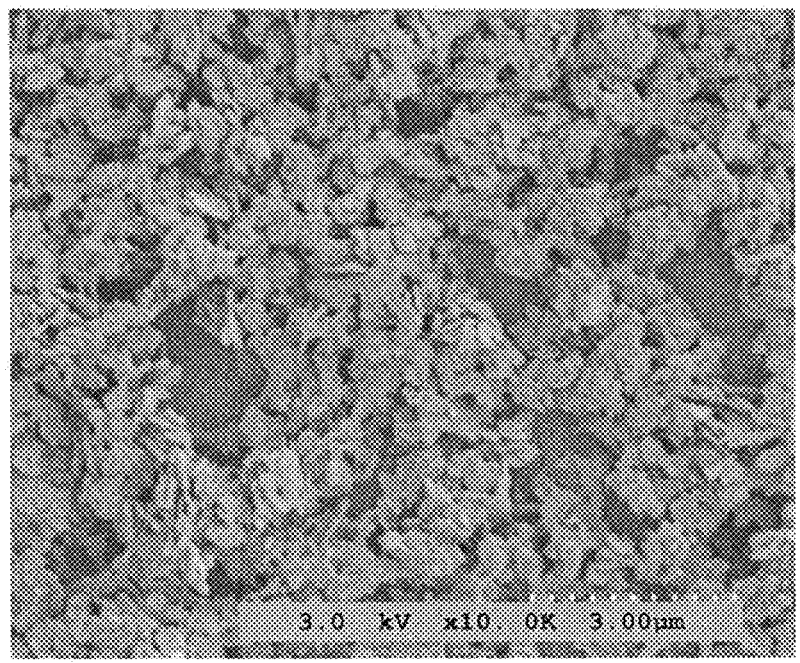
FIG. 2 is a scanning electron microscope image of the coating film of the flaky powder of zinc oxide subjected to surface treatment with silicone (methyl hydrogen polysiloxane) obtained in Production Example 3.

The SEM images are each shown in FIG. 1 (Production Example 2) and FIG. 2 (Production Example 3). As is apparent from FIGS. 1 and 2, it is found that the flaky powder of zinc oxide subjected to surface treatment with alkylsilane (octyltriethoxysilane) used in the present invention has achieved a highly uniform coating film, whereas the flake-like zinc oxide powder subjected to surface treatment with silicone (methyl hydrogen polysiloxane) has failed to have a uniform coating film with some powder aggregates and fine holes.

Examples 1 to 8 and Comparative Examples 1 to 9

Water-in-oil emulsified cosmetic compositions having the blending compositions as shown in the following Table 2 were prepared by the following production method. The thus-obtained emulsified cosmetic compositions were subjected to an evaluation test as described below. The evaluation results are shown in Table 2 altogether.
(Evaluation Method)
(1) UV-Protective Effect
The SPF values were measured using an SPF analyzer (manufactured by Optometrics) and are shown according to the following criteria.
[Evaluation Criteria for UVB-Protective Effect]
A: an SPF value of 40 or more
B: an SPF value of 30 or more and less than 40
C: an SPF value of 20 or more and less than 30
D: an SPF value of less than 20
[Evaluation Criteria for UVA-Protective Effect]
a: a T (UVA) of less than 20% b: a T (UVA) of 20% or more and less than 25%
c: a T (UVA) of 25% or more

Here, T (UVA) is defined by the following formula.

$$T(UVA)(\%) = \frac{\sum_{320}^{400} T_\lambda \times \Delta\lambda}{\sum_{320}^{400} \Delta\lambda}$$

$\begin{cases} T_\lambda: \text{Permeability}(\%) \text{ at a given wavelength } \lambda \\ \Delta\lambda: \text{Interval between measured wavelengths} \end{cases}$ (2) Feeling Upon Application An expert panel of 10 people was assigned to each evaluation item (however, panelists may overlap depending on the item). They actually used the preparations and evaluated them for "presence of a transparent feeling after application" and "smoothness upon application" according to the following evaluation criteria. The evaluation results are shown based on the sum score of all the panelists according to the following criteria.

[Evaluation criteria of the panelist]

| Evaluation criteria | score |
|---|---|
| Felt a high effect | 5 |
| Felt an effect | 4 |
| Felt a slight effect | 3 |
| Felt only a subtle effect | 2 |
| Felt no effect | 1 |

[Evaluation Result of the Feeling after Application]
A: a sum score of 40 or more
B: a sum score of 35 or more and less than 40
C: a sum score of 25 or more and less than 35
D: a sum score of less than 25

(3) Long-Term Stability

Each sample was stored in a constant temperature bath at 60° C. for one month. The condition after one month was observed and judged using the following judgment criteria.

[Judgment Criteria for Storage Stability]
A: No change
B: a slight change in viscosity was observed
C: an apparent change in viscosity was observed
D: separation was observed

TABLE 2

| | Component | | Example 1 | Example 2 | Example 3 | Example 4 | Example 5 | Example 6 | Example 7 | Example 8 | Comparative Example 1 |
|---|---|---|---|---|---|---|---|---|---|---|---|
| 1 | (A) | Alkylsilane-treated flaky powder of zinc oxide (Production Example 2) | 10 | 10 | 10 | 6 | 10 | 5 | 10 | 8 | — |
| 2 | | Flake-like zinc oxide (Production Example 1) | — | — | — | — | — | — | — | — | 15 |
| 3 | | Silicone-treated flaky powder of zinc oxide (Production Example 3) | — | — | — | — | — | — | — | — | — |
| 4 | (B) | Alkylsilane-treated fine particle zinc oxide powder (Production Example 4) | — | 5 | — | 10 | 10 | — | — | — | — |
| 5 | (B) | Silicone-treated fine particle zinc oxide powder (Production Example 5) | — | — | 5 | — | — | 10 | 1 | 5 | — |
| 6 | | Silicone-treated fine particle titanium dioxide powder (Production Example 6) | — | — | — | — | — | — | — | 2 | — |
| 7 | | Dimethylpolysiloxane | 5 | 5 | 5 | 5 | 5 | 5 | 5 | 5 | 5 |
| 8 | | Methylcyclopolysiloxane | 30 | 30 | 30 | 30 | 30 | 30 | 30 | 30 | 30 |
| 9 | | Perfluoroalkyl/polyoxyalkylene co-modified silicone (Note 1) | 1 | 1 | 1 | 1 | 1 | 1 | 1 | 1 | 1 |
| 10 | | Sorbitan monoisostearate | 1 | 1 | 1 | 1 | 1 | 1 | 1 | 1 | 1 |
| 11 | (D) | 2-Ethylhexyl paramethoxycinnamate | 7.5 | 7.5 | 7.5 | 7.5 | 7.5 | 7.5 | 7.5 | 7.5 | 7.5 |
| 12 | (D) | 2-(4-Diethylamino-2-hydroxybenzoyl)-hexyl benzoate | 1 | 1 | 1 | 1 | 1 | 1 | 1 | 1 | 1 |
| 13 | | Ethanol | 5 | 5 | 5 | 5 | 5 | 5 | 5 | 5 | 5 |
| 14 | | Purified water | Balance | Balance | Balance | Balance | Balance | Balance | Balance | Balance | Balance |
| | | Blending ratio (flake-like zinc oxide/fine particle zinc oxide) | — | 2 | 2 | 0.6 | 1 | 0.5 | 10 | 1.6 | — |
| Evaluation | | | | | | | | | | | |
| Feeling upon application | (Smoothness upon application) | | B | A | A | B | A | B | B | A | B |
| | (Transparent feeling after application) | | A | A | A | A | A | C | C | A | D |
| Long-term stability | | | A | A | B | A | A | B | A | B | D |
| UVA-protective effect | | | b | a | a | a | a | b | a | a | c |
| UVB-protective effect | | | C | A | A | B | A | B | A | A | D |

| | Component | | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|---|
| 1 | (A) | Alkylsilane-treated flaky powder of zinc oxide (Production Example 2) | — | — | — | — | — | — | — | — |
| 2 | | Flake-like zinc oxide (Production Example 1) | — | — | — | — | 10 | 10 | — | — |
| 3 | | Silicone-treated flaky powder of zinc oxide (Production Example 3) | 15 | — | — | — | — | — | 10 | 10 |

TABLE 2-continued

|   |     | Component | | | | | | | | |
|---|-----|-----------|---|---|---|---|---|---|---|---|
| 4 | (B) | Alkylsilane-treated fine particle zinc oxide powder (Production Example 4) | — | — | — | — | 5 | — | — | — |
| 5 | (B) | Silicone-treated fine particle zinc oxide powder (Production Example 5) | — | 15 | — | 10 | — | 5 | 5 | — |
| 6 |     | Silicone-treated fine particle titanium dioxide powder (Production Example 6) | — | — | 15 | 5 | — | — | — | 5 |
| 7 |     | Dimethylpolysiloxane | 5 | 5 | 5 | 5 | 5 | 5 | 5 | 5 |
| 8 |     | Methylcyclopolysiloxane | 30 | 30 | 30 | 30 | 30 | 30 | 30 | 30 |
| 9 |     | Perfluoroalkyl/polyoxyalkylene co-modified silicone (Note 1) | 1 | 1 | 1 | 1 | 1 | 1 | 1 | 1 |
| 10 |    | Sorbitan monoisostearate | 1 | 1 | 1 | 1 | 1 | 1 | 1 | 1 |
| 11 | (D) | 2-Ethylhexyl paramethoxycinnamate | 7.5 | 7.5 | 7.5 | 7.5 | 7.5 | 7.5 | 7.5 | 7.5 |
| 12 | (D) | 2-(4-Diethylamino-2-hydroxybenzoyl)-hexyl benzoate | 1 | 1 | 1 | 1 | 1 | 1 | 1 | 1 |
| 13 |    | Ethanol | 5 | 5 | 5 | 5 | 5 | 5 | 5 | 5 |
| 14 |    | Purified water | Balance | Balance | Balance | Balance | Balance | Balance | Balance | Balance |
| Blending ratio (flake-like zinc oxide/fine particle zinc oxide) | | | — | — | — | — | 2 | 2 | 2 | — |
| Evaluation | | | | | | | | | | |
| Feeling upon application | (Smoothness upon application) | | B | D | D | D | C | C | C | B |
|  | (Transparent feeling after application) | | C | B | B | B | D | D | D | C |
| Long-term stability | | | C | B | C | C | D | D | C | C |
| UVA-protective effect | | | b | b | c | b | c | c | b | c |
| UVB-protective effect | | | C | C | B | C | D | D | C | B |

(Note 1):
FPD-6131 (manufactured by Shin-Etsu Chemical Co., Ltd.)
(Production Method)
(A): Components (1) to (12) are dissolved by heating at 70° C. and homogeneously mixed.
(B): A component (14) is heated to 70° C.
(C): While stirring A, B is gradually added for preliminary emulsification.
(D): C is cooled to 35° C., and then a component (13) is gradually added thereto, followed by stirring. The resulting mixture is homogenously mixed with a homomixer, deaerated, and then cooled to give an emulsified cosmetic composition.

As is clear from Table 1, the emulsified cosmetic composition containing the silane compound-treated flake-like zinc oxide powder (A) of the present invention is found to have not only a high UV-protective effect but also good long-term stability, a good transparent feeling, and a good feeling upon application. The emulsified cosmetic composition of the present invention produced by using the powder (A) in combination with the fine particle zinc oxide (B) exhibited a particularly outstanding effect.

Examples 9 to 10 and Comparative Examples 10 to 11

Oil-in-water emulsified cosmetic compositions having the blending compositions as shown in the following Table 3 were prepared by the following production method. The thus-obtained emulsified cosmetic compositions were evaluated for a feeling upon application (the absence of a sticky feeling and the presence of a moist feeling), long-term stability, and a UV-protective effect based on the aforementioned evaluation criteria. The evaluation results are shown in Table 3 altogether.

TABLE 3

|   |     | Component | Example 9 | Example 10 | Comparative Example 10 | Comparative Example 11 |
|---|-----|-----------|-----------|------------|------------------------|------------------------|
| 1 | (A) | Alkylsilane-treated flaky powder of zinc oxide (Production Example 2) | 10 | 10 | — | — |
| 2 | (B) | Alkylsilane-treated fine particle zinc oxide powder (Production Example 4) | 5 | 5 | — | 15 |
| 3 | (D) | 2-Ethylhexyl paramethoxycinnamate | 7.5 | 7.5 | 7.5 | 7.5 |
| 4 | (D) | 2-(4-Diethylamino-2-hydroxybenzoyl)-hexyl benzoate | 0.5 | 0.5 | 0.5 | 0.5 |
| 5 |     | Isocetyl myristate | 3 | 3 | 3 | 3 |
| 6 |     | Decamethylcyclopentasiloxane | 5 | 5 | 5 | 5 |
| 7 |     | Dimethylpolysiloxane | 5 | 5 | 5 | 5 |
| 8 |     | Sodium acrylate-sodium acryloyldimethyl taurate copolymer (Note 1) | 3 | 3 | 3 | 3 |
| 9 |     | Disodium edetate | 0.02 | 0.02 | 0.02 | 0.02 |
| 10 | (E) | Xanthan gum | — | 0.1 | 0.1 | 0.1 |
| 11 | (E) | Hyaluronic acid | 0.01 | 0.01 | — | — |
| 12 |    | Purified water | Balance | Balance | Balance | Balance |
| 13 |    | Ethanol | 10 | 10 | 10 | 10 |
| 14 |    | Phenoxyethanol | 0.05 | 0.05 | 0.05 | 0.05 |
| 15 |    | Paraben | 0.1 | 0.1 | 0.1 | 0.1 |

TABLE 3-continued

|  | Example | | Comparative Example | |
|---|---|---|---|---|
| Component | 9 | 10 | 10 | 11 |
| Evaluation | | | | |
| Feeling upon (absence of sticky feeling) application | A | A | B | D |
| (moist feeling) | A | A | B | C |
| Long-term stability | B | A | B | B |
| UVA-protective effect | a | a | c | b |
| UVB-protective effect | A | A | D | B |

(Note 1):
SIMULGEL EG (manufactured by SEPPIC)
(Production Method)
(A): Components (1) to (7) are dissolved by heating at 70° C. and homogeneously mixed.
(B): Components (8) to (12) are homogeneously dissolved and mixed at 70° C.
(C): While stirring B, A is gradually added for preliminary emulsification.
(D): C is cooled to 40° C., and then components (13) to (15) are gradually added thereto, followed by stirring. The resulting mixture is homogenously mixed with a homomixer, deaerated, and then cooled to give an emulsified cosmetic composition.

Problems of an ultraviolet absorber, 2-(4-diethylamino-2-hydroxybenzoyl hexyl benzoate, which absorbs wavelengths in the UV-A region, are that it poorly dissolves in an oil agent or a solvent, becomes unstable when used in combination with a metal oxide, and has a strong sticky feeling. However, the use of the configuration of the present invention enabled a good feeling upon application, while maintaining long-term stability.

Examples 11 to 20 and Comparative Examples 12 to 18

Water-in-oil emulsified cosmetic compositions having the blending compositions as shown in the following Table 4 were prepared by the following production method. The thus-obtained emulsified cosmetic compostions were subjected to an evaluation test as described below. The evaluation results are shown in Table 4 altogether.
(Evaluation Method)
A UV-protective effect and long-term stability were evaluated in the same manner as in Examples 1 to 10 described above.
(1) Evaluation of the Smoothness of the Coating Film
[Test Method]
The average dynamic friction coefficient was measured using a handy tribomaster (manufactured by Trinity lab., type: TL-201-Sa).
[Measurement Method]
A test sample was put onto a model skin (Bioplate: manufactured by Beaulax Co., Ltd.) in an amount of 4 mg/cm$^2$ and applied so that the sample uniformly adapted to the skin. After drying at room temperature for 60 minutes, a test coating film was obtained. The average dynamic friction coefficient of each sample coating film was measured with a friction meter (TL201Ts: manufactured by Trinity lab.) under the conditions of a moving rate of 500 mm/minute, measurement distance: 50 mm one way, and load: 200 g/cm$^2$. It is to be noted that the smaller the number, the better smoothness the sample coating film has, and the results are shown according to the following criteria.
[Evaluation Criteria]
a: the average dynamic friction coefficient is less than 0.6
b: the average dynamic friction coefficient is 0.6 or more and less than 0.7
c: the average dynamic friction coefficient is 0.7 or more
(2) Evaluation of Cosmetic Durability (Water Repellency/Oil Repellency), and a Transparent Feeling after Application
An expert panel of 10 people was assigned to each evaluation item (however, panelists may overlap depending on the item). They actually used the preparations and evaluated them for "cosmetic durability (water repellency/oil repellency)" and "a transparent feeling after application" according to the following evaluation criteria. The evaluation results are shown based on the sum score of all the panelists according to the following criteria.

| [Evaluation criteria of the panelist] | |
|---|---|
| Evaluation criteria | score |
| Felt a high effect | 5 |
| Felt an effect | 4 |
| Felt a slight effect | 3 |
| Felt only a subtle effect | 2 |
| Felt no effect | 1 |

[Evaluation Result of a Feeling Upon Application]
A: a sum score of 40 or more
B: a sum score of 35 or more and less than 40
C: a sum score of 25 or more and less than 35
D: a sum score of less than 25

TABLE 4

|  | Component | Example | | | | | | | | |
|---|---|---|---|---|---|---|---|---|---|---|
|  |  | 11 | 12 | 13 | 14 | 15 | 16 | 17 | 18 | 19 |
| 1 | (A) Alkylsilane-treated flaky powder of zinc oxide (Production Example 2) | 15 | 15 | 10 | 10 | 10 | 10 | 6 | 10 | 5 |
| 2 | Flake-like zinc oxide (Production Example 1) | | | | | | | | | |

TABLE 4-continued

| | Component | | | | | | | | | |
|---|---|---|---|---|---|---|---|---|---|---|
| 3 | Silicone-treated flaky powder of zinc oxide (Production Example 3) | | | | | | | | | |
| 4 (C) | Alkylsilane-treated fine particle zinc oxide powder (Production Example 4) | | | | 5 | 5 | | 10 | 10 | |
| 5 (C) | Silicone-treated fine particle zinc oxide powder (Production Example 5) | | | | | | 5 | | | 10 |
| 6 (C) | Silicone-treated fine particle titanium dioxide powder (Production Example 6) | | | 5 | | | | | | |
| 7 | Dimethylpolysiloxane | 5 | 5 | 5 | 5 | 5 | 5 | 5 | 5 | 5 |
| 8 | Methylcyclopolysiloxane | 30 | 30 | 30 | 30 | 30 | 30 | 30 | 30 | 30 |
| 9 (B) | Polyoxyethylene-methylpolysiloxane copolymer (Note 1) | — | 1 | — | — | 1 | — | — | — | — |
| 10 (B) | Perfluoroalkyl/polyoxyalkylene co-modified silicone (Note 2) | 1 | — | 1 | 1 | — | 1 | 1 | 1 | 1 |
| 11 | Sorbitan monoisostearate | 1 | 1 | 1 | 1 | 1 | 1 | 1 | 1 | 1 |
| 12 (D) | 2-Ethylhexyl paramethoxycinnamate | 7.5 | 7.5 | 7.5 | 7.5 | 7.5 | 7.5 | 7.5 | 7.5 | 7.5 |
| 13 (D) | 2-(4-Diethylamino-2-hydroxybenzoyl)-hexyl benzoate | 1 | 1 | 1 | 1 | 1 | 1 | 1 | 1 | 1 |
| 14 | Ethanol | 5 | 5 | 5 | 5 | 5 | 5 | 5 | 5 | 5 |
| 15 | Purified water | Balance | Balance | Balance | Balance | Balance | Balance | Balance | Balance | Balance |
| | Blending ratio (flake-like metal oxide/fine particle metal oxide) | — | — | 2 | 2 | 2 | 2 | 0.6 | 1 | 0.5 |
| | Evaluation | | | | | | | | | |
| Feeling upon application | (Smoothness of coating film) | a | a | a | a | a | a | b | a | b |
| | (Cosmetic durability) | A | B | B | A | B | A | A | B | B |
| | (Transparent feeling after application) | B | B | A | A | B | A | B | B | B |
| | Long-term stability | A | B | B | A | B | B | A | A | B |
| | UVA-protective effect | a | a | a | a | a | a | a | a | b |
| | UVB-protective effect | A | A | A | A | A | A | A | A | A |

| | | Example | Comparative Example | | | | | | |
|---|---|---|---|---|---|---|---|---|---|
| | Component | 20 | 12 | 13 | 14 | 15 | 16 | 17 | 18 |
| 1 (A) | Alkylsilane-treated flaky powder of zinc oxide (Production Example 2) | 10 | — | — | 10 | — | — | — | — |
| 2 | Flake-like zinc oxide (Production Example 1) | | | | | 10 | 10 | | |
| 3 | Silicone-treated flaky powder of zinc oxide (Production Example 3) | | | | | | | 10 | 10 |
| 4 (C) | Alkylsilane-treated fine particle zinc oxide powder (Production Example 4) | | 15 | | | 5 | 5 | | |
| 5 (C) | Silicone-treated fine particle zinc oxide powder (Production Example 5) | 1 | | | | | | | |
| 6 (C) | Silicone-treated fine particle titanium dioxide powder (Production Example 6) | | | 15 | | | | 5 | 5 |
| 7 | Dimethylpolysiloxane | 5 | 5 | 5 | 5 | 5 | 5 | 5 | 5 |
| 8 | Methylcyclopolysiloxane | 30 | 30 | 30 | 30 | 30 | 30 | 30 | 30 |
| 9 (B) | Polyoxyethylene-methylpolysiloxane copolymer (Note 1) | — | — | — | — | — | — | — | — |
| 10 (B) | Perfluoroalkyl/polyoxyalkylene co-modified silicone (Note 2) | 1 | 1 | 1 | — | 1 | — | 1 | — |
| 11 | Sorbitan monoisostearate | 1 | 1 | 1 | 1 | 1 | 1 | 1 | 1 |
| 12 (D) | 2-Ethylhexyl paramethoxycinnamate | 7.5 | 7.5 | 7.5 | 7.5 | 7.5 | 7.5 | 7.5 | 7.5 |
| 13 (D) | 2-(4-Diethylamino-2-hydroxybenzoyl)-hexyl benzoate | 1 | 1 | 1 | 1 | 1 | 1 | 1 | 1 |
| 14 | Ethanol | 5 | 5 | 5 | 5 | 5 | 5 | 5 | 5 |
| 15 | Purified water | Balance | Balance | Balance | Balance | Balance | Balance | Balance | Balance |
| | Blending ratio (flake-like metal oxide/fine particle metal oxide) | 10 | — | — | — | 2 | 2 | 2 | 2 |
| | Evaluation | | | | | | | | |
| Feeling upon application | (Smoothness of coating film) | a | c | c | b | c | c | c | c |
| | (Cosmetic durability) | B | C | C | C | D | D | D | D |
| | (Transparent feeling after application) | B | B | B | C | D | D | C | C |
| | Long-term stability | A | A | A | D | D | D | B | D |

TABLE 4-continued

| | | | | | | | | |
|---|---|---|---|---|---|---|---|---|
| UVA-protective effect | a | b | c | b | c | c | b | b |
| UVB-protective effect | B | C | A | C | D | D | C | C |

(Note 1): BY22-008M manufactured by Dow Corning Toray Co., Ltd.
(Note 2): FPD-6131, manufactured by Shin-Etsu Chemical Co., Ltd.

(Production Method)
(A): Components (1) to (13) are dissolved by heating at 70° C. and homogeneously mixed.
(B): A component (15) is heated to 70° C.
(C): While stirring A, B is gradually added for preliminary emulsification.
(D): C is cooled to 35° C., to which a component (14) is gradually added, followed by stirring. The resulting mixture is homogenously mixed with a homomixer, deaerated, and then cooled to give a water-in-oil emulsified cosmetic composition.

Examples 21 to 23 and Comparative Examples 19 to 21

Water-in-oil emulsified cosmetic compositions having the blending compositions as shown in the following Table 5 were prepared by the following production method. The thus-obtained emulsified cosmetic compositions were evaluated for a feeling upon application (smoothness of the coating film) and long-term stability based on the aforementioned evaluation criteria. The evaluation results are shown in Table 5 altogether.

(Production Method)
A: Components (1) to (10) are dissolved by heating at 70° C. and homogeneously mixed.
B: A component (12) is heated to 70° C.
C: While stirring A, B is gradually added for preliminary emulsification.
D: C is cooled to 35° C., and then a component (11) is gradually added thereto, followed by stirring. The resulting mixture is homogenously mixed with a homomixer, deaerated, and then cooled to give a water-in-oil emulsified cosmetic composition.

TABLE 5

| | Component | Example 21 | Example 22 | Example 23 | Comparative Example 19 | Comparative Example 20 | Comparative Example 21 | Comparative Example 22 |
|---|---|---|---|---|---|---|---|---|
| 1 (A) | Alkylsilane-treated flaky powder of zinc oxide (Production Example 2) | 10 | 10 | 15 | — | — | — | 10 |
| | Flake-like zinc oxide (Production Example 1) | | | | | 10 | | |
| 2 (C) | Alkylsilane-treated fine particle zinc oxide powder (Production Example 4) | 5 | 5 | — | — | 5 | 15 | 5 |
| 3 | Dimethylpolysiloxane | 5 | 5 | 5 | 5 | 5 | 5 | 5 |
| 4 | Methylcyclopolysiloxane | 30 | 30 | 30 | 30 | 30 | 30 | 30 |
| 5 (B) | Perfluoroalkyl/polyoxyalkylene co-modified silicone (Note 2) | 1 | 1 | 1 | 1 | 1 | 1 | — |
| 6 | Sorbitan monoisostearate | 1 | 1 | 1 | 1 | 1 | 1 | 1 |
| 7 (D) | 2-Ethylhexyl paramethoxycinnamate | — | 7.5 | 7.5 | 7.5 | 7.5 | 7.5 | 7.5 |
| 8 (D) | 2-(4-Diethylamino-2-hydroxybenzoyl)-hexyl benzoate | — | 1 | 1 | 1 | 1 | 1 | 1 |
| 9 (D) | Octocrylene (Note 3) | | | 0.5 | | | | |
| 10 (D) | 2,4-bis{[4-(2-ethylhexyloxy)-2-hydroxy]phenyl}-6-(4-methoxyphenyl)-1,3,5-triazine (Note 4) | | | 0.5 | | | | |
| 11 | Ethanol | 5 | 5 | 5 | 5 | 5 | 5 | 5 |
| 12 | Purified water | Balance | Balance | Balance | Balance | Balance | Balance | Balance |
| | Blending ratio (flake-like metal oxide/fine particle metal oxide) | 2 | 2 | — | | 2 | | 2 |
| | Evaluation | | | | | | | |
| | Feeling upon application (Smoothness of coating film) | a | a | a | c | c | c | b |
| | Long-term stability | A | A | A | C | D | B | D |

(Note 3): Parsol 340, manufactured by DSM Nutrition Japan K.K.
(Note 4): Tinosorb S, manufactured by Ciba Specialty Chemicals Inc.

Problems of an ultraviolet absorber, diethylamino hydroxybenzoyl hexyl benzoate, which absorbs wavelengths in the UV-A region, are that it poorly dissolves in an oil agent or a solvent, becomes unstable when used in combination with metal oxide, and has a strong sticky feeling. However, the invention of the present application achieved a good feeling upon application, while maintaining long-term stability.

Hereinbelow, Formulation Examples of the emulsified cosmetic composition of the present invention will be shown. All of the following emulsified cosmetic compositions have a high transparent feeling and a high UV-protective effect with excellent long-term stability and an excellent feeling upon application.

Formulation Example 1

Water-In-Oil Emulsified Sunscreen Cream

| | (% by weight) |
|---|---|
| Component (A) | |
| 1. Alkylsilane-treated flaky powder of zinc oxide (Production Example 2) | 10.0 |
| Component (B) | |
| 2. Silicone-treated fine particle zinc oxide powder (Production Example 5) | 5.0 |
| Component (D) | |
| 3. Diethylamino hydroxybenzoyl hexyl benzoate | 1.0 |
| 4. Decamethylcyclopentasiloxane | 25.0 |
| 5. Dimethicone (SH200C Fluid 2 cs, manufactured by Dow Corning Toray Co., Ltd.) | 7.0 |
| Component (C) | |
| 6. Polyether-modified silicone (BY22-008M, manufactured by Dow Corning Toray Co., Ltd., in terms of pure content) | 0.6 |
| Component (D) | |
| 7. 2-Ethylhexyl paramethoxycinnamate | 4.0 |
| 8. Sorbitan monoisostearate | 1.0 |
| 9. Methylphenylpolysiloxane (FZ-209, manufactured by Dow Corning Toray Co., Ltd.) | 3.0 |
| 10. Isononyl isononanoate | 1.0 |
| 11. Squalane | 1.0 |
| 12. 1,3-Butylene glycol | 5.0 |
| 13. Yellow iron oxide | 0.5 |
| 14. Sodium chloride | 1.0 |
| Component (E) | |
| 15. Sodium hyaluronate | 0.1 |
| 16. Hydrolyzed collagen | 0.01 |
| 17. Stearyl glycyrrhetinate | 0.1 |
| 18. Phenoxyethanol | 0.3 |
| 19. Fragrance | 0.1 |
| 20. Purified water | Balance |

Formulation Example 2

Oil-In-Water Emulsified Sunscreen Cosmetic Base

| | (% by weight) |
|---|---|
| Component (A) | |
| 1. Alkylsilane-treated flaky powder of zinc oxide (Production Example 2) | 10.0 |
| Component (B) | |
| 2. Silicone-treated fine particle zinc oxide powder (Production Example 5) | 10.0 |
| Component (D) | |
| 3. Diethylamino hydroxybenzoyl hexyl benzoate | 1.0 |
| 4. 2-Ethylhexyl paramethoxycinnamate | 5.0 |
| 5. Octyldodecyl myristate | 2.0 |
| 6. Sorbitan stearate | 0.3 |
| Component (C) | |
| 7. Polyoxyethylene-methylpolysiloxane copolymer (Silicone KF-6017, Shin-Etsu Chemical Co., Ltd.) | 1.0 |
| 8. Dimethicone (6 cs) | 3.0 |
| 9. Decamethylcyclopentasiloxane | 10.0 |
| 10. Squalane | 3.0 |
| 11. Polymethylsilsesquioxane (with an average primary particle diameter of 4.5 μm) | 5.0 |
| 12. Ethanol | 10.0 |
| 13. Sodium stearoxy PG-hydroxyethylcellulose sulfonate (POIZ 310, manufactured by Kao Corporation) | 0.5 |
| 14. Disodium edetate | 0.02 |
| 15. Glycerin | 5.0 |
| 16. 1,3-butylene glycol | 5.0 |
| 17. Acerola extract (trade name: Acerola extract BG25 (manufactured by Maruzen Pharmaceuticals Co., Ltd.)) | 1.0 |
| 18. Prune extract (trade name: Prune extract WC (manufactured by Maruzen Pharmaceuticals Co., Ltd.)) | 0.5 |
| Component (E) | |
| 19. Hyaluronic acid | 0.5 |
| 20. Fragrance | 0.1 |
| 21. Phenoxyethanol | 0.3 |
| 22. Purified water | Balance |

Formulation Example 3

Water-in-Oil Sunscreen Emulsified Cosmetic Composition

| | (% by weight) |
|---|---|
| Component (A) | |
| Alkylsilane-treated flaky powder of zinc oxide (Production Example 2) | 10.0 |
| Component (B) | |
| Alkylsilane-treated fine particle zinc oxide powder (Production Example 4) | 5.0 |
| Silicone-treated fine particle titanium dioxide powder (Production Example 6) | 5.0 |
| Component (C) | |
| PEG-9 polydimethylsiloxyethyl dimethicone (KF-6028, manufactured by Shin-Etsu Chemical Co., Ltd.) | 2.0 |
| Dimethicone (2.0 cs) | 10.0 |
| Methyl trimethicone | 20.0 |
| Component (D) | |
| Octyl methoxycinnamate | 7.5 |
| 2-(4-Diethylamino-2-hydroxybenzoyl)-hexyl benzoate | 1.0 |
| Organo-modified bentonite | 0.5 |
| Isononyl isononanoate | 3.0 |
| Ethanol | 5.0 |
| Preservative | q.s. |
| Purified water | Balance |

Formulation Example 4

Water-in-Oil Emulsified Cream

| | (% by weight) |
|---|---|
| Component (A) | |
| Alkylsilane-treated flaky powder of zinc oxide (Production Example 2) | 8.0 |
| Component (B) | |
| Silicone-treated fine particle zinc oxide powder (Production Example 5) | 5.0 |

-continued

| | (% by weight) |
|---|---|
| Component (D) | |
| Diethylamino hydroxybenzoyl hexyl benzoate | 1.0 |
| Decamethylcyclopentasiloxane | 25.0 |
| Dimethicone (6 cs) | 3.0 |
| (SH200C Fluid 6 cs, manufactured by Dow Corning Toray Co., Ltd.) | |
| Component (C) | |
| Polyether-modified silicone | 0.6 |
| (BY22-008M, manufactured by Dow Corning Toray Co., Ltd., in terms of pure content) | |
| Component (D) | |
| 2-Ethylhexyl paramethoxycinnamate | 7.5 |
| Sorbitan monoisostearate | 1.0 |
| Methylphenylpolysiloxane | 3.0 |
| (FZ-209, manufactured by Dow Corning Toray Co., Ltd.) | |
| Isononyl isononanoate | 1.0 |
| Squalane | 1.0 |
| 3-butylene glycol | 7.0 |
| Xylobiose | 1.0 |
| (trade name: xylobiose mixture, manufactured by Hokkaido Sugar Co., Ltd.) | |
| Kiwi extract | 0.5 |
| (trade name: Pharcolex kiwi, manufactured by Ichimaru Pharcos Co., Ltd.) | |
| Sodium chloride | 1.0 |
| Component (E) | |
| Sodium hyaluronate | 0.1 |
| Hydrolyzed collagen | 0.01 |
| Stearyl glycyrrhetinate | 0.1 |
| Phenoxyethanol | 0.3 |
| Fragrance | 0.1 |
| Purified water | Balance |

Also, the compositions of the fragrances used in the aforementioned Examples and Formulation Examples are shown in Table 6.

TABLE 6

| Fragrance formulation | | | |
|---|---|---|---|
| Component | ‰ by weight | Component | ‰ by weight |
| Terpineol | 10.00 | Vanillin | 2.00 |
| Terpinyl acetate | 2.00 | Ethyl vanillin | 0.10 |
| Cepionate | 60.00 | Muscone | 0.50 |
| Methyl dihydrojasmonate | 250.00 | Ethylene brassylate | 42.00 |
| Indole | 0.05 | 4,6,6,7,8,8-Hexamethyl-1,3,4,6,7,8-hexahydro-cyclopentabenzopyran | 60.00 |
| 2-Methyl-3-(3,4-methylenedioxy-phenyl)-propanal | 3.00 | Cyclopentadecanolide | 20.00 |
| Hydroxycitronellal | 20.00 | Ambrettolide | 1.00 |
| Hydroxycitronellol | 10.00 | γ-Undecalactone | 0.40 |
| p-t-Butyl-α-methylhydrocinnamic aldehyde | 35.00 | γ-Decalactone | 0.10 |
| 4-(4-Hydroxy-4-methyl-pentyl)-3-cyclohexen-1-carboxaldehyde | 75.00 | 4-(4-Hydroxyphenyl)-2-butanone | 0.50 |
| 3-Methyl-5-phenylpentanol | 20.00 | Musk ketone | 0.10 |
| Phenylethyl alcohol | 10.00 | Skatole | 0.01 |
| α-Ionone | 10.00 | cis-Jasmon | 0.05 |
| β-Ionone | 20.00 | Phenylethyl acetate | 0.10 |
| γ-Methylionone | 10.00 | Civetone | 0.20 |
| Dihydro-β-ionone | 25.00 | γ-Nonalactone | 0.05 |
| Benzyl salicylate | 150.00 | α-Santalol | 0.20 |
| cis-3-Hexenyl salicylate | 30.00 | β-Santalol | 0.20 |
| Eugenol | 0.80 | Eugenyl acetate | 0.10 |
| Cinnamic alcohol | 5.00 | α-Hexyl cinnamic aldehyde | 20.00 |
| Cinnamic aldehyde | 0.50 | α-Damascone | 0.04 |
| Guaiol acetate | 1.00 | β-Damascone | 0.02 |
| Guaiol | 0.50 | β-Damascenone | 0.01 |
| Cedrenyl acetate | 5.00 | δ-Damascone | 0.01 |
| Cedryl methyl ketone | 30.00 | Rose absolute | 0.50 |
| 6,7-Dihydro-1,1,2,3,3-pentamethyl-4(5H)-indan | 2.00 | Rose oil | 4.50 |
| Vetiver acetate | 10.00 | Sandalwood oil | 2.00 |
| 3-Methyl-5-(2,3,3-trimethyl-3-cyclopenten-1-yl)-pentan-2-ol | 2.00 | Labdanum absolute | 0.05 |
| 2-Ethyl-4-(2,3,3-trimethyl-3-cyclopenten-1-yl)-2-buten-1-ol | 0.80 | Cistus absolute | 0.01 |
| Isobornyl cyclohexanol | 35.00 | Vetiver oil | 0.50 |
| Heliotropin | 10.00 | Guaiac wood oil | 0.10 |
| Coumarin | 2.00 | Total | 1000.00 |

The invention claimed is:

1. An emulsified cosmetic composition comprising a powder which is produced by subjecting a zinc oxide powder (A) having an average particle diameter of 0.1 to 1 μm, an average particle thickness of 0.01 to 0.2 μm, and an average aspect ratio of 3 or more to surface treatment with a silane or silazane compound having a $C_{1-20}$ alkyl or fluoroalkyl group and having reactivity with an inorganic oxide, and further comprising a zinc oxide powder (B) having an average particle diameter of 0.01 to 1 μm and an average aspect ratio of less than 3, wherein a weight ratio of powder (A) to the powder (B), (A/B), is from 0.6-10.

2. The emulsified cosmetic composition according to claim 1, wherein the silane or silazane compound is at least one selected from the group consisting of hexyltrimethoxysilane, octyltrimethoxysilane, decyltrimethoxysilane, octadecyltrimethoxysilane, octyltriethoxysilane, trifluoropropyltrimethoxysilane, heptadecafluorodecyltrimethoxysilane, hexamethyldisilazane, and octyldisilazane.

3. The emulsified cosmetic composition according to claim 1, wherein the silane or silazane compound is at least one selected from the group consisting of octyltriethoxysilane and octyltrimethoxysilane.

4. The emulsified cosmetic composition according to claim 1, further comprising a polyether-modified silicone (C).

5. The emulsified cosmetic composition according to claim 4, wherein the polyether-modified silicone is a perfluoroalkyl/polyoxyalkylene co-modified silicone.

6. The emulsified cosmetic composition according to claim 1, further comprising an organic ultraviolet absorber (D).

7. The emulsified cosmetic composition according to claim 6, wherein the organic ultraviolet absorber (D) is at least one selected from the group consisting of 2-hydroxy-4-methoxybenzophenone, 2-hydroxy-4-methoxybenzophenone-5-sulfonic acid, 2,2'-dihydroxy-4,4'-dimethoxybenzophenone, disodium 2,2'-dihydroxy-4,4'-dimethoxy-5,5'-disulfobenzophenone, 2,4-dihydroxybenzophenone, 2,2',4,4'-tetrahydroxybenzophenone, 4-tert-butyl-4'-methoxy-dibenzoylmethane, 2,4,6-trianilino-p-(carbo-2'-ethylhexyl-1'-oxy)-1,3,5-triazine, menthyl anthranilate, 2-(2-hydroxy-5- methylphenyl)benzotriazole, and 2-(4-diethylamino-2-hydroxybenzoyl)-hexyl benzoate.

8. The emulsified cosmetic composition according to claim 6, wherein the organic ultraviolet absorber (D) is 2-(4-diethylamino-2-hydroxybenzoyl)-hexyl benzoate.

9. The emulsified cosmetic composition according claim 1, further comprising at least one polysaccharides (E) selected from the group consisting of pullulan, dextran, cyclosophoran, laminarin, schizophyllan, lentinan, arabinogalactan, barley glucan, lichenan, succinoglycan, xyloglucan, locust bean gum, xanthan gum, chitosan, pustulan, carrageenan, hyaluronic acid, and a salt thereof.

10. The emulsified cosmetic composition according to claim 9, wherein the polysaccharide (E) is hyaluronic acid, an alkali metal salt of hyaluronic acid, or xanthan gum.

* * * * *